United States Patent [19]

Boiko et al.

[11] 3,954,565

[45] May 4, 1976

[54] APPARATUS FOR CULTIVATING MICROORGANISMS

[76] Inventors: Ivan Danilovich Boiko, Varshavskoe shosse, 180, korpus 2, kv. 73; Anatoly Vladimirovich Naidin, Smolenskaya ulitsa, 10, kv. 159, both of Moscow, U.S.S.R.

[22] Filed: June 11, 1975

[21] Appl. No.: 585,791

Related U.S. Application Data

[63] Continuation of Ser. No. 239,164, March 29, 1972, abandoned.

[52] U.S. Cl. ............................... 195/142; 195/139; 195/143
[51] Int. Cl.[2] ........................................... C12B 1/14
[58] Field of Search.... 195/109, 127, 139, 141–144; 259/8, 22–24, 107; 261/87

[56] References Cited
UNITED STATES PATENTS

| 1,779,181 | 10/1930 | McDonald | 261/87 |
| 3,400,051 | 9/1968 | Hofschneider | 195/142 |

*Primary Examiner*—A. Louis Monacell
*Assistant Examiner*—R. B. Penland
*Attorney, Agent, or Firm*—Haseltine, Lake & Waters

[57] ABSTRACT

An apparatus for cultivating microorganisms, comprising ejectors adapted to disperse and intermix the culture liquid and aerating agent, the ejectors being rotatable and located in a container for the culture liquid having a diffuser for the directional flow of the latter.

6 Claims, 3 Drawing Figures

APPARATUS FOR CULTIVATING MICROORGANISMS

CROSS-RELATED APPLICATION

This application is a continuation of application Ser. No. 239,164 filed Mar. 29, 1972, now abandoned.

The present invention relates to apparatus for cultivating microorganisms, e.g., yeasts by the aerobic method on various kinds of carbon nutrients such as purified liquid petroleum hydrocarbons.

Apart from the microbiological industry, the present invention can find application also in the food and pharmaceutical industries, in the production of fermenting preparations, antibiotics and the like production processes.

Additionally, the invention is also applicable to the chemical, petrochemical, paint-and-varnish industries for carrying out mass-exchange processes, as well as in a complex of treatment arrangements.

Known heretofore is a prior-art apparatus for cultivating microorganisms, comprising ejectors for dispersing and intermixing culture liquid and an aerating agent, located in a container provided with a diffuser for a directional flow of the culture liquid.

For being saturated with oxygen, the culture liquid in said apparatus is discharged along the pipes and is pump-fed to the stationary ejectors in whose mixing chambers the culture liquid comes into contact with an oxygen-containing aerating agent, such as air fed via the gas duct. The mixing chambers of the ejectors communicate with the apparatus via the lateral wall and are so arranged with respect to the apparatus that the oxygen-enriched culture liquid is fed thereinto tangentially and is spread throughout the interior space of the apparatus by means of a mechanical agitator or due to autorotation of the stream of liquid around the axis of symmetry of the cylindrical apparatus.

However, autorotation of the stream of the gas-saturated culture liquid around the smooth-walled diffuser fails to provide an effective concentration averaging, this being due to a substantial reduction of the energy of the stream during its flow through the liquid medium, said energy drop resulting from the turbulent flow the liquid.

To provide a directional flow of the gas-saturated liquid fed by the ejectors, the apparatus is provided with a vertical smooth-walled diffuser along whose outside surface ascends the aerated culture liquid having a lower specific gravity.

The spent aerating agent is separated from the liquid in the top portion of the apparatus and the higher specific gravity deaerated liquid flows in a stream along the inner diffuser surface downwards whence it is taken by the pump to be repeatedly fed into the ejectors.

The stationary ejectors provided in said apparatus predetermine the admission of the aerated liquid at a single point of the apparatus, i.e., at the place of the ejector location, thereby establishing a clearly marked gradient of concentrations of the liquid-dissolved oxygen over the interior space of the apparatus.

A continuous progressive pumping-out of the deaerated liquid from the apparatus and its subsequent feeding into the ejectors acts adversely on the microorganisms being cultivated due to these being vehiculated in an oxygenless medium in conjunction with the simultaneous local disturbance of certain decisive parameters of cultivation, such as temperature, the value of the pH (hydrogen ions concentration) of the nutrient medium, etc.

It is worth special notice that when using pumps for feeding the culture liquid to the ejectors, stalling of the pumps is liable to occur due to the presence of froth in the culture liquid due to specific features inherent in the microorganism cultivating process; such failure of the pumps results in surging or pulsations in the delivery of the liquid phase and, moreover, in the adversely affected general efficacy of the ejector operation.

Furthermore, the use of pipes along which the culture liquid is pump-fed results in that unfavorable zones arise during the delivery of the culture liquid therealong, said zones being depleted in oxygen and featuring uncontrolled values of pH and temperatures of cultivation; additionally, the provision of metal pipes in the apparatus makes it more metal consuming.

It is an object of the present invention to provide an apparatus for cultivating microorganisms which would be capable of utilizing a high mass-transfer coefficient obtained from the use of the ejectors, to enable a high concentration of oxygen dissolved in the culture liquid to be obtained throughout the volume of the apparatus.

It is another object of the present invention to provide an apparatus which makes it possible to obviate even a short-time withdrawal of the culture liquid from the apparatus.

It is a further object of the present invention to provide an apparatus which is simpler in construction as compared to the known apparatus of the same type.

Among the other objects of the present invention, may be mentioned the provision of such an apparatus that enables effective power consumption and were used production output with the power input remaining at the same level and reduced metal consumption of the apparatus.

These objects are satisfied by the provision of an apparatus for cultivating microorganisms, incorporating ejectors for the culture liquid and an aerating agent to disperse and intermix, said ejectors being located within the container for the culture liquid which is provided with a diffuser for a directional flow of the culture liquid, wherein, according to the invention said ejectors are made horizontally rotatable to take the liquid into the ejector which makes it possible to admit the oxygen-enriched culture liquid to pass over the entire volume of the ejectors with subsequent averaging of the concentration of the dissolved oxygen during vertical ascension of the aerated liquid.

To impart rotation to the ejectors the apparatus includes a hollow body of revolution located inside the container beneath the diffuser and to which the ejectors are secured.

It is expedient that the hollow body of revolution incorporate a cylindrical portion for the intake of the culture liquid, arranged concentrically with the diffuser at a clearance therewith, and another portion shaped as a toroid and coupled to the former, the toroidal-shaped portion being adapted to feed the culture liquid to the ejectors, said ejectors being mounted in the lateral surface of the toroidal portion such that their mixing chamber is directed opposite to the sense of rotation of the ejectors, thereby establishing an ascending flow of the oxygen-enriched culture liquid throughout the peripheral section of the apparatus.

The ejectors may be mounted in the lateral surface of the toroidal portion either at an angle or tangentially therewith in the plane of rotation of the ejectors, thus enabling optimum conditions of formation and discharge of a gas-liquid stream from the ejectors.

The mixing chamber may be arranged tangentially to the outside surface of the toroidal portion in the plane of rotation of the ejectors, thus increasing the chamber length.

The culture-liquid-to-ejector feeding portion can have a rectangular box-shaped duct whose outside surface serves to guide the culture liquid to the ejectors, while the interior space serves to feed the aerating agent.

Due to the centrifugal effect, said duct contains all the liquid to flow from the culture-liquid intake portion to the ejectors, thus establishing a constant pressure head before the ejectors; moreover, gas bubbles, due their being less dense as compared to the bulk of the continuous culture liquid, are expelled to the center of the hollow body of revolution, wherefrom they are eliminated by self-floating upwards. Thus, fed to the ejectors is practically the bulk of the uniform culture liquid which is conducive to higher efficiency of the apparatus.

The apparatus may likewise be equipped with vertically arranged baffle plates that partition the interior space of the apparatus across the inside surface of the liquid-culture container and the outside surface of the diffuser so as to accelerate the escape of the aerating agent which promotes sorption of oxygen by the culture liquid and renders an effective outflow of the spent oxygen-depleted gas.

Apart from that discussed above, the apparatus may be provided with vertically arranged baffle plates that partition the interior space of the diffuser to prevent formation of a suction vortex in the culture liquid at the location of its inlet and make said liquid continuous and uniform.

Said baffle plates render the liquid more uniform, thus facilitating separation and self-floating of the gas bubbles from the diffuser.

When using a large-volume apparatus, it is expedient to divide the liquid culture intake portion into two zones symmetrical with respect to the axis of rotation of the ejectors to provide bilateral intake of the culture liquid, thus enabling the liquid culture circulation rate to be made faster whenever necessary.

Given below is a detailed description of a specific embodiment of the present invention with reference to the appended drawings. wherein.

Figure 1:
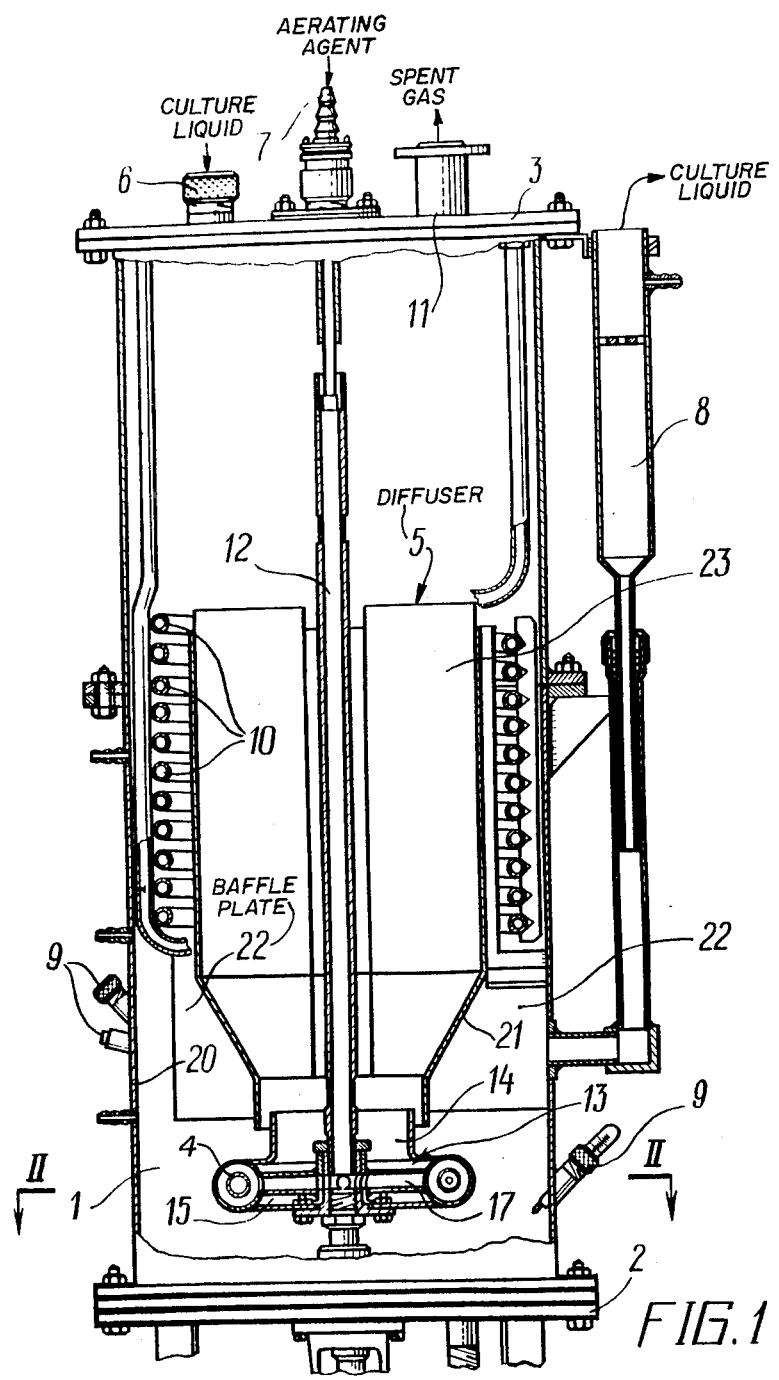
FIG. 1 is a side view of the apparatus, according to the invention, partly broken away and in section.

Reference being now directed to FIG. 1, the herein-disclosed apparatus for cultivating microorganisms is essentially a cylindrical container 1 to hold the culture liquid the container, having a flat bottom-plate 2 and a flat cover-plate 3.

Figure 2:
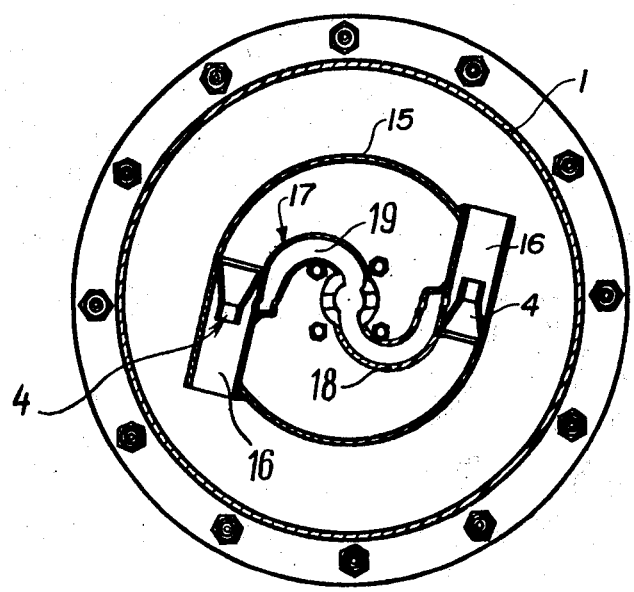
FIG. 2 is a section taken along line II—II in FIG. 1.
Figure 3:
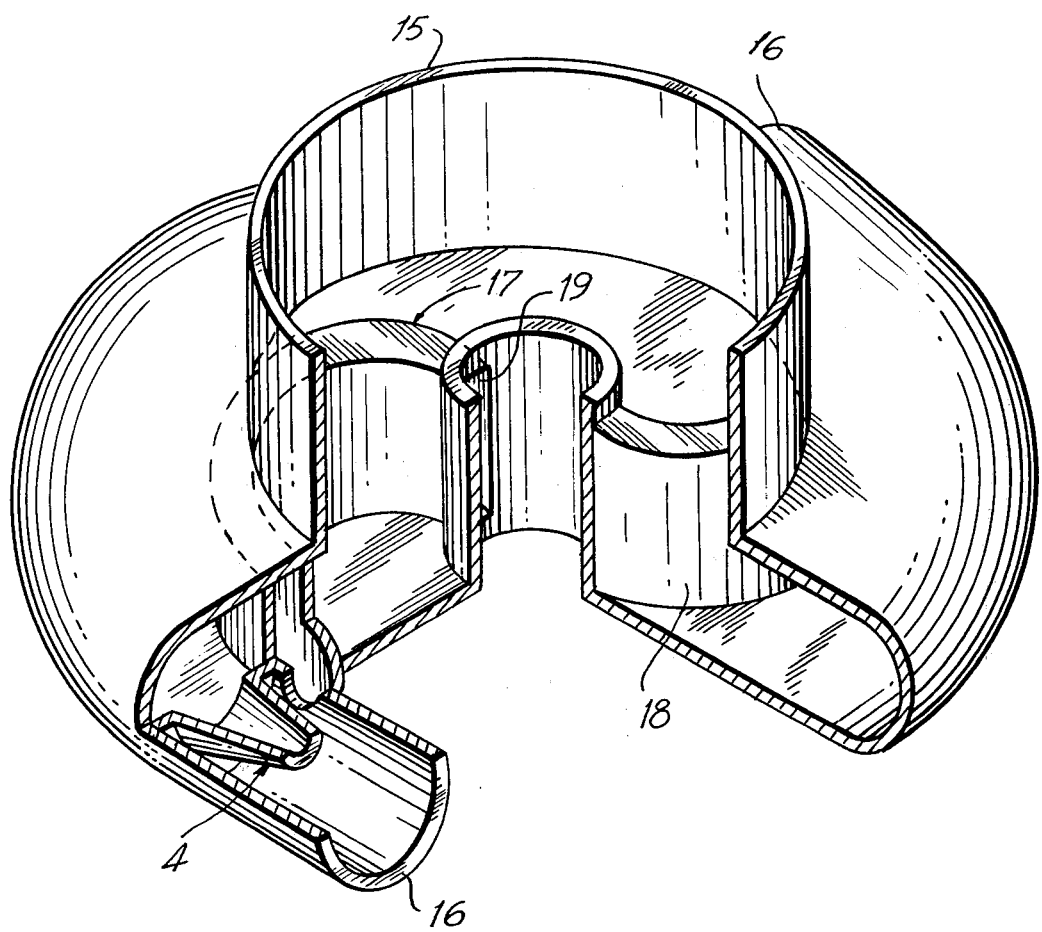
FIG. 3 is a perspective view partly broken away showing the hollow body and the ejector of FIG. 2.

Accommodated in the container 1 are ejectors 4 (FIG. 2) adapted to disperse and intermix the culture liquid and aerating agent. Additionally, the container is provided with a stationary diffuser (FIG. 1) for the culture liquid directional flow.

To feed the culture-liquid components and the aerating agent into the apparatus, respective inlet unions 6 and 7 are provided in the cover-plate 3 of the apparatus.

To discharge the culture liquid from the apparatus, an overflow device 8 is provided communicating with the container 1 at the bottom of the apparatus.

To check and control the technological parameters of the cultivation process, i.e., $t°$, pH, P, etc., provision is made for unions 9 made in the lateral surface of the container 1, through which checking and control are carried out by means of appropriate devices.

To control the temperature of the culture liquid, the apparatus is provided with a heat exchanger 10.

To discharge spent gas from the apparatus, an outlet union 11 is provided in the cover plate 3 of the apparatus.

The aerating agent is fed to the ejectors 4 via an air duct 12.

A hollow body of revolution 13 is provided in the container 1 for rotating the ejectors 4. The hollow body of revolution 13 has a cylindrical portion 14 for receiving the culture liquid, and a toroidal portion 15 coupled with the portion 14, for feeding the culture liquid to the ejectors.

The culture-liquid receiving, portion 14 is arranged concentrically with respect to the diffuser 5 at a clearance therewith which obviates great hydrodynamical resistance to the culture liquid circulation in the vertical plane.

The ejectors 4 are mounted in the lateral surface of the toroidal portion 15 in such a way that their mixing chambers 16 (FIG. 2) are directed oppositely to the direction of rotation of the ejectors 4. The ejectors may be mounted either tangentially to the lateral surface of the culture-liquid feeding portion or at an angle thereto which makes it possible to establish optimum conditions for the gas-liquid stream to discharge from the ejectors.

The mixing chambers 16 for the ejectors is arranged tangentially to the outside surface of the toroidal portion in the plane of rotation of the ejectors, thus increasing its geometrical length without increasing the overall hydrodynamical resistance of the apparatus.

The torodial portion 15 incorporates a rectangular box-shaped air duct 17 whose outside surface 18 serves to guide the culture liquid to the ejectors, while the interior space 19 thereof serves to feed the aerating agent to the mixing chambers 16.

The duct 17 due to the centrifugal effect, constrains all the liquid to flow from the receiving portion 14 to the ejectors, thus establishing a constant pressure head before the ejector, 4 while gas bubbles contained in the liquid, due to their being less dense as compared to the mess of the culture liquid, are expelled to the center of the hollow body of- revolution, wherefrom they are eliminated by self-floating upwards. Thus, the bulk of the uniform culture liquid is practically fed to the ejectors, thereby enhancing the working efficiency thereof.

Vertical baffle plates 22 are provided between an inside surface 20 of the container 1 and an outside surface 21 of the diffuser 5 so as to partition the interior space of the apparatus and to accelerate the escape of the aerating agent which makes it possible to promote the process of sorption of oxygen by the culture liquid by virtue of the complete gas expelling principle and, consequently, to ensure an effective outflow of the spent oxygen-depleted gas.

Vertical baffle plates 23 are mounted in the interior space of the diffuser 5 to prevent the formation of a suction vortex in the culture liquid and aerating agent which is liable to arise within the culture-liquid and aerating agent receiving portion, thus adding to the degree of uniformity and continuity of the liquid and facilitating the process of separation and self-floating of gas bubbles from the diffuser.

The liquid-culture receiving portion 14 may be divided into two zones arranged symmetrically with respect to the axis of rotation of the ejectors. Such a constructional feature of the apparatus makes possible a bilateral intake of the culture liquid and is practicable in large-volume apparatus.

The herein-disclosed apparatus operates as follows.

The components of the culture liquid are filled into the container 1 via the inlet union 6 to one half the container capacity; then the seeding mass of the microorganisms is inoculated on the culture liquid and the drive is actuated to effect rotation of the ejectors.

This causes the culture liquid, due to centrifugal force established by the duct 18, to be force-fed via the ejectors 4 into the mixing chambers 16, wherein suction is created depending upon the rotational speed of the drive. Due to the suction in the mixing chambers 16, the aerating agent is drawn from the space 19, the air duct 12 and the union 7 into the mixing chamber 16.

Due to fine dispersity of the "liquid-gas" phases, the culture liquid while in the mixing chamber 16 becomes saturated with oxygen from the aerating agent. Then the oxygen-saturated culture liquid ascends throughout the interior space between the outside surface 21 of the diffusor 5 and the inside surface 20 of the container 1 to successively pass the sections of the heat exchanger 10. Upon arrival of the gas-saturated culture liquid onto the baffle plates 22, enlarging of gas bubble occurs and, as a result, an accelerated floating-up of said bubbles from the culture liquid, takes place which promotes the mass-exchange process, i.e., oxygen dissolution in the liquid phase. The spent aerating agent is discharged via the outlet union 11.

The culture liquid depleted in the aerating agent, while flowing along the interior space of the diffuser 5, passes across its entire cross-sectional area in a downflow towards the liquid-receiving portion 14. The suction vortex arising in the liquid is suppressed by the baffle plates 23. The overflow device 8 for a continuous removal of the culture liquid is set for a definite liquid level and due to an uninterrupted feed of the liquid-culture components, a continuous cultivation process of microorganisms is conducted upon reaching a preset concentration thereof. The process of accumulation of microorganisms is carried out according to the aforedescribed technique without taking-out the culture liquid and feeding the components thereof.

What is claimed is:

1. An apparatus for cultivating microorganisms, comprising: a container for the culture liquid; means to feed the culture liquid into said container; an aerating agent supply means; rotatable ejector means located inside said container for receiving the culture liquid and aerating agent to disperse and intermix the same; means to impart rotation to said ejector means; said container including a diffuser therein adapted to provide a directional flow of the culture liquid to the ejector means, said rotatable ejector means comprising a hollow body located inside the container beneath the diffuser and including a cylindrical-shaped portion for receiving the culture liquid in the container and arranged concentrically below the diffuser in spaced relation therewith, a toroidal portion coupled to said cylindrical portion for receiving the culture liquid from said cylindrical portion, ejectors on said toroidal portion, and a mixing chamber extending in prolongation of each said ejector and having an inlet connected to the aerating agent supply means, said ejectors being mounted on said toroidal portion within the mixing chamber, said mixing chamber extending from the ejectors in a direction opposite to the direction of rotation thereof.

2. An apparatus as claimed in claim 1, wherein the ejectors are mounted tangentially on the toroidal portion in the plane of rotation of said ejectors.

3. An apparatus as claimed in claim 1, wherein the rotatable ejector means includes a rectangular box-shaped duct having outside surfaces cooperating with the toroidal portion to guide the culture liquid to the ejectors, said duct feeding the aerating agent to the mixing chamber.

4. An apparatus as claimed in claim 1, comprising vertically arranged baffle plates to partition the interior space of the container between the inside surface of the container and the outside surface of the diffuser to accelerate the discharge of spent aerating agent.

5. An apparatus as claimed in claim 1, comprising vertically arranged baffle plates to partition the interior space of the diffuser to prevent formation of a suction vortex in the culture liquid at the place of its inlet into said hollow body and to make said liquid continuous and uniform.

6. An apparatus as claimed in claim 1, wherein the culture liquid receiving portion is divided into two zones symmetrical with respect to the axis of rotation of the ejectors so as to provide a bilateral intake of the culture liquid.

* * * * *